United States Patent [19]

Alperovich et al.

[11] Patent Number: 4,724,834

[45] Date of Patent: Feb. 16, 1988

[54] CRYOGENIC-AND-ULTRASONIC SCALPEL

[75] Inventors: Boris I. Alperovich; Ljutsia M. Paramonova; Gennady I. Tjulkov; Valery I. Soloviev; Alexandr I. Paramonov, all of Tomsk, U.S.S.R.

[73] Assignee: Tomsky Gosudarstvenny Meditsinsky Institut, Momsk, U.S.S.R.

[21] Appl. No.: 900,457

[22] Filed: Aug. 26, 1986

[30] Foreign Application Priority Data

Nov. 20, 1985 [SU] U.S.S.R. .............................. 397388[I]

[51] Int. Cl.⁴ .............................................. A61B 17/36
[52] U.S. Cl. .......................... 128/303.1; 128/DIG. 27
[58] Field of Search .................. 128/24 A, 24.1, 24.2, 128/303.1, 399–402, DIG. 27; 73/642

[56] References Cited

U.S. PATENT DOCUMENTS

| | | | |
|---|---|---|---|
| 3,636,943 | 1/1972 | Balamuth | 128/303.1 |
| 3,786,814 | 1/1974 | Armad | 128/303.1 |
| 3,918,442 | 11/1975 | Nikolaev et al. | 128/303.1 |
| 3,942,519 | 3/1976 | Shock | 128/303.1 |
| 4,582,979 | 7/1985 | Marchenko et al. | 128/303.1 |
| 4,609,368 | 9/1986 | Dotson | 128/24 A |

FOREIGN PATENT DOCUMENTS

| | | | |
|---|---|---|---|
| 460869 | 4/1975 | U.S.S.R. | 128/303.1 |
| 556797 | 6/1977 | U.S.S.R. | 128/303.1 |
| 1153901 | 5/1985 | U.S.S.R. | 128/303.1 |

OTHER PUBLICATIONS

"Cryosurgery Imaging with Ultrasound", Rubinsky et al., Mechanical Engineering, Jan. 1986.

Primary Examiner—Kyle L. Howell
Assistant Examiner—Max F. Hindenburg
Attorney, Agent, or Firm—Burgess, Ryan and Wayne

[57] ABSTRACT

A cryogenic-and-ultrasonic scalpel comprises a body, a source of ultrasonic vibrations accommodated in the body, a transformer connected to the source of ultrasonic vibrations, and a tubular heat exchanger adapted for refrigerant to admitted to and withdrawn from the scalpel blade, the heat exchanger being accommodated in the body and made as at least two intercommunicating coaxial tubes. The blade and the vibration transferring member are connected to the outside tube, ultrasonic vibrations being imparted to the outside tube and further to the blade through the transformer.

10 Claims, 2 Drawing Figures

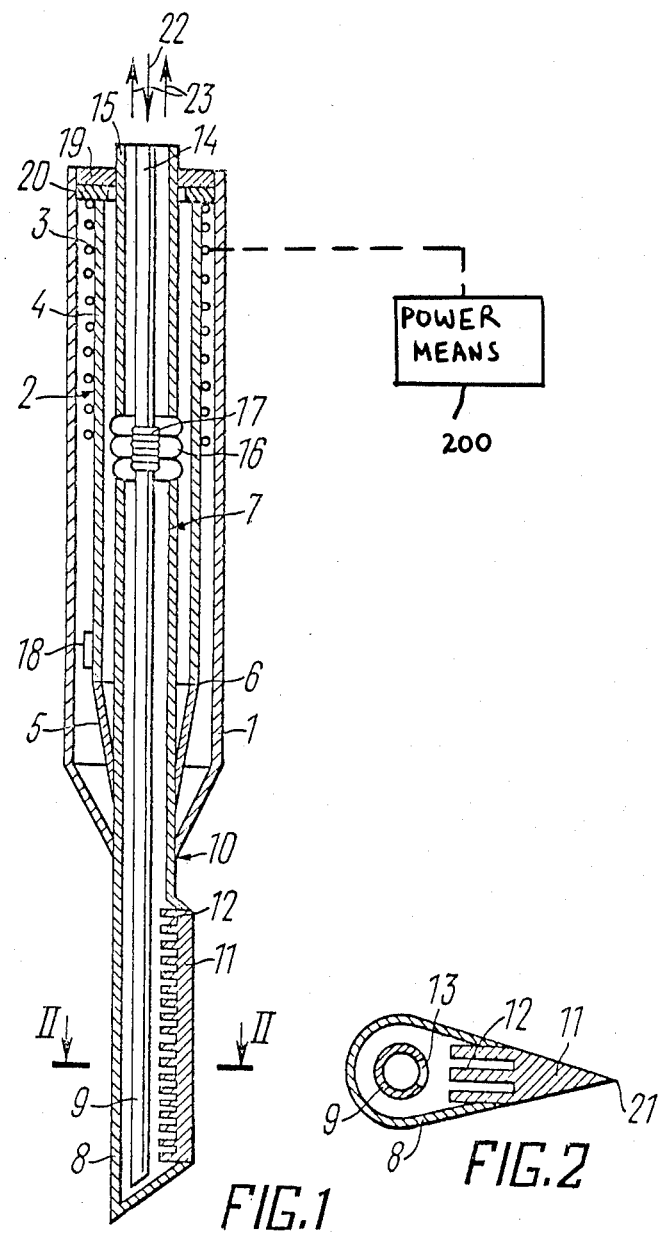

CRYOGENIC-AND-ULTRASONIC SCALPEL

FIELD OF THE INVENTION

The invention relates generally to surgical instruments and more specifically it concerns cryogenic-and-ultrasonic scalpels.

The invention can find application for surgery on soft tissues and parenchymatous organs, i.e., the liver, pancreas, kidneys, lungs, spleen, as well as in neurosurgery.

BACKGROUND ART

Known in the present state of the art are cryogenic-and-ultrasonic surgical instruments, particularly, probes which comprise a mechanism joining the working portion with the source of ultrasonic vibrations, a jacket for refrigerant to pass, interposed between the instrument base and the source of ultrasonic vibrations, and a nozzle located at the inlet of the refrigerant to the instrument (cf., e. G., USSR Inventor's Certificate No. 460,869 Int. Cl. A61F 7/00, 1975, Bulletin No. 7, inventors A. A. Pisarevsky et al.). However, the instrument is unsuitable for surgery as not capable of dissecting tissues.

There is known a cryogenic-and-ultrasonic scalpel, comprising a body accommodating a source of ultrasonic vibrations, a blade connected to the source of ultrasonic vibrations through a vibration transferring member and a tubular heat exchanger for refrigerant to admitted to and withdrawn from the blade. The best exchanger is fashioned as a U-shaped tube installed with a possibility of thermal contact with the blade lateral surface and is connected to the refrigerant admission and withdrawal pipes through bellows located within the zone of a standing wave arising when the blade is connected to the source of ultrasonic vibrations. The tubes of the heat exchanger taper towards the cutting edge of the scalpel. (cf., e.g., USSR Inventor's Certificate No. 825056 Int.Cl. A61B 17/36, 1981, Bulletin No. 16, inventors L. M. Paramonova et al.).

Disadvantages inherent in the aforesaid cryogenic-and-ultrasonic scalpel reside in a low hemostatic effect and inadequate tissue dissection rate in surgery on soft tissues and parenchymatous organs, such as the liver or pancreas, due to too low refrigerating capacity of the U-shaped tubular heat exchanger. These disadvantages stem from the fact the blade features direct and thermal contact with the transformer at the point of their interconnection. In this case, a considerable part of the heat evolved by the vibration transferring member and the source of ultrasonic vibrations due to a great loss of conversion of electric ultrasonic power into mechanical power, is translated to the blade, thus causing its temperature rise. As a result, the refrigerating capacity of the U-shaped heat exchanger which is in thermal contact not only with the blade but also with the abundantly blood-supplied organ being operated (e.g., the liver), happens to be insufficient, especially in cases of prolonged surgery, thus causing tissue sticking to the blade, reduced tissue dissection rate and adversely affected hemostatic therapeutic effect.

Moreover, the U-shape of the heat exchanger featuring the refrigerant admission and withdrawal pipes spaced somewhat apart renders the instrument too unwieldy and hence inconvenient in operation.

SUMMARY OF THE INVENTION

It is an object of the invention to provide a cryogenic-and-ultrasonic scalpel, wherein the tissue being dissected would be prevented from sticking to the blade.

It is another object of the invention to retain such a tissue dissection rate that is equal to the dissection rate obtained with a conventional scalpel.

It is a further object of the invention to provide a higher hemostatic therapeutic effect in the course of surgery.

It is still another object of the invention to maintain the temperature of the instrument below 130° C. in order to eliminate tissue sticking to the blade.

It is yet another object of the invention to provide a scalpel that would be of low bulk and handy in operation.

It is a further object of the invention to reduce traumatic lesion inflicted upon the tissues of the organs operated upon.

It is an additional object of the invention to provide a scalpel that would be instrumental in establishing a maximum depth of tissue freezing of 2 mm, that is, in eliminating temperature traumatization of tissue.

It is also an object of the invention to reduce the amount of heat inflow to the blade and hence to increase the refrigerating capacity of the instrument.

It is likewise an object of the invention to provide an automatic adjustment of frequency of ultrasonic vibrations due to reduced loss of conversion of ultrasonic electric power into mechanical power.

These objects are accomplished due to the fact that in a cryogenic-and-ultrasonic scalpel, comprising a body accommodating a source of ultrasonic vibrations, a blade connected to the source of ultrasonic vibrations through a vibration transforming member, and a tubular heat exchanger for refrigerant to admitted to and withdrawn from the blade, according to the invention, the tubular heat exchanger is fashioned as at least two coaxial intercommunicating tubes, and the vibration transferring member is connected to the outside tube of the tubular heat exchanger so as to impart ultrasonic vibrations to the above said tube.

It is expedient that the vibration transferring member be made as a hollow annular body whose through bore accommodates the outside coaxially arranged tube of the tubular heat exchanger in the form, of, e.g., a hollow cone frustum the greater base of which is connected to the source of ultrasonic vibrations, while the lesser base is rigidly linked to the outside tube of the tubular heat exchanger so as to impart ultrasonic vibrations to the scalpel blade.

A longitudinal slit may be made in the outside tube of the tubular heat exchanger for the scalpel blade to be tightly held therein, while the blade surface facing into the bore of the outside tube may be shaped as at least a single-row comb.

It is desirable that the holes in the inside tube of the tubular heat exchanger be directed towards the comb-shaped blade portion.

It is also practicable that an ultrasonic vibration pickup be connected to the source of ultrasonic vibrations and be accommodated inside the body so as to provide control of the frequency of ultrasonic vibrations, said ultrasonic vibration pickup being expedient to be located within the antinode zone of a sound wave arising from excitation of the source of ultrasonic vibrations.

BRIEF DESCRIPTION OF THE DRAWINGS

Other objects and advantages of the present invention will become apparent hereinbelow from a consideration of some specific embodiments thereof with reference to the accompanying drawings, wherein:

FIG. 1 is a general longitudinal sectional view of a cryogenic-and ultrasonic scalpel, according to the invention; and FIG. 2 is a section taken through the scalpel of FIG. 1 along the line II—II therein.

DETAILED DESCRIPTION OF THE INVENTION

The cryogenic-and-ultrasonic scalpel of the invention comprises a body 1, a source 2 of ultrasonic vibrations accommodated in the body 1 and provided with an energizing coil 3 and a magnetostrictive element 4. As is commonly known, a power means 200 supplies power to energize coil 3 at a desired frequency so as to cause vibration of magnetostrictive element 4, the rate of vibration depending upon the frequency of energization of coil 3.

Connected to the source 2 is a vibration transferring member 5 which is made as a hollow annular body the most efficient shape of the member 5 proving to be a hollow cone frustum whose greater base 6 is connected to the source 2. Accommodated inside the body 1 in a through bore of the member 5 is a tubular heat exchanger 7 adapted to admit and withdraw a refrigerant. The heat exchanger is constituted by at least two intercommunicating coaxial tubes 8 and 9, of which the outside tube 8 is connected to a lesser base 10 of the transformer 5 so as to transmit ultrasonic vibrations to said tube 8.

The heat exchanger 7 may have more than two of such tubes although the number of tubes depends on the requirements of to the refrigerating capacity of the heat exchanger 7. The accompanying drawings represent an embodiment of the heat exchanger 7 incorporating two tubes, however, three, four, or more tubes may be employed to good advantage.

A longitudinal slit is made in the outside tube 8 of the heat exchanger 7 on its section protruding beyond the body 1, a blade 11 (FIG. 2) being tightly held in said slit.

The surface of the blade 11 (FIG. 1) that faces into the bore of the tube 8 is shaped as at least a single-row comb 12 for the sake of increased contact areas of the blade 11 with the refrigerant. With a view to further increasing the aforesaid contact area, the comb 12 may be made of a multirow design, e.g., three-rows as shown in FIG. 2.

A plurality of holes 13 are made in the inside tube 9 of the heat exchanger 7 at the level of the comb 12 for the refrigerant to pass.

The inside tube 9 (FIG. 1) and the outside tube 8 of the heat exchanger 7 are connected respectively to sleeves 14 and 15 through bellows 17 and 16.

Connected to the source 2 (FIG. 1) is an ultrasonic vibration pickup 18 which is accommodated in the body 1 and provides for controlling of the frequency of ultrasonic vibrations that is, it is well known that pickup 18 controls power means 200 to control the frequency of energization of coil 3. The pickup 18 is most efficient when installed within the antinode zone of an ultrasonic wave arising from excitation of the source 2.

The body 1 is tightly closed with a cover 19 seated in gasket 20.

In the embodiment considered herein the blade 11 is held in place with a cutting edge 21 extending outwardly.

The cryogenic-and-ultrasonic scalpel is prepared for operation as follows.

The refrigerant is fed along the inlet sleeve 14 through the bellows 17, in the direction of an arrow 22, to the heat exchanger 7, whereupon it flows along its inside tube 9 and upon emerging from the hole 13, hits the teeth of the comb 12 of the blade 11.

The resultant vapour-liquid mixture is discharged from the heat exchanger 7 along its outside tube 8 through the bellows 16 and the sleeve 15 as indicated with arrows 23.

The working temperature setting time of the cryogenic-and-ultrasonic scalpel, when using liquid nitrogen at 80° K. as a refrigerant, ranges within 3 and 5 min at a positive pressure in the feed reservoir equal to $0.2 \times 10^5$ or $0.5 \times 10^5$ Pa. While getting cooled the blade is first covered with hoar-frost, and on reaching a temperature of 80° K. the atmospheric gases are liquefied on the blade, which is manifested by formation of a thin film of liquid air on the outside tube 8 of the heat exchanger 7 extending from the body 1 and on the blade 11 tightly held in the longitudinal slit of said tube.

Once the working temperature of the scalpel has been attained, the source 2 of ultrasonic vibrations is energized. To obtain the maximum vibration amplitude of the blade 11, the frequency of the source 2 is automatically adjusted for the resonant level with the aid of the ultrasonic vibration pickup 18. This in turn leads to the maximum vibration amplitude of the blade 11, eliminates sticking of the tissues operated upon to the blade 11 and enhances the hemostatic effect produced, whereupon the organ is operated upon.

In the case of surgery on the soft tissues or parenchymatous organs, the working temperature of the blade is within 120° K. since the inflow of cold to the blade 11 from the heat exchanger 7 exceeds the inflow of heat from the organ being operated on. A high hemostatic effect is observed even when the blade 11 is introduced completely into the organ being operated on so that the tissue in contact with the portion of the outside tube 8 extending from the heat exchanger 7 and carrying the blade 11 tightly held in the longitudinal slit, is cooled at the highest rate. The tissue dissection rate is adjusted by an appropriately selected refrigerant pressure, whereby sticking of the tissue of the organ operated upon to the blade 11 is eliminated. This in turn makes it possible to dissect tissues with the proposed cryogenic-and-ultrasonic scalpel at a rate equal to that of a conventional surgical scalpel even in cases of prolonged surgery on such organs as the liver and pancreas.

Thanks to the fact that the blade 11 is tightly held in the longitudinal slit of the outside tube 8 of the heat exchanger 7 extending from the body 1 and that the blade surface facing into the bore of the heat exchanger tube is shaped as the multi-row comb 12 whose teeth face towards the inside tube 9 of the heat exchanger 7 provided with the holes 13 spaced throughout the length of the comb 12, there occurs more efficient cooling of the blade 11 of the cryogenic-and-ultrasonic scalpel due to an increased area of heat transfer between the refrigerant and the blade 11. Moreover, the additional provision of the pickup 18 on the source 2 of ultrasonic vibrations within the antinode zone of an ultrasonic wave resulting from excitation of said source makes possible an automatic adjustment of the frequency of the source 2 of ultrasonic vibrations in the course of the scalpel operation. This in turn results in a 3 to 5 fold reduction of heat evolution from the vibration transferring member 5 (due to lower loss of conversion of ultrasonic electric power into mechanical power, that is, in decreased heat inflows to the blade 11. Apart from this, the tissue of the organ operated upon is prevented from sticking to the blade 11, the rate of tissue dissection is increased and the therapeutic hemostatic effect is enhanced.

Provision of the heat exchanger 7 in the shape of the coaxially arranged tubes, the outside tube 8 and the inside tube 9, both being accommodated in the through bore of the hollow member 5, reduces overall dimensions of the scalpel and makes manipulations with it more convenient, without injuring the tissues of the parenchymatous organ being operated. Besides, no tissue sticking to the blade 11 occurs, the dissection rate is increased and any postoperative complications become less possible.

The present cryogenic-and-ultrasonic scalpel has been tested experimentally on twelve test animals, wherein resection of the liver of different sections has been performed. It is established that the present scalpel, after having reached the working temperature, is capable of tissue dissecting at a rate of a conventional scalpel, involves no tissue sticking to the blade 11 and produces hematostatis on parenchymatous vessels having a diameter up to 2 mm.

With the use of the present cryogenic-and-ultrasonic scalpel there have been performed a total of seven liver resections under clinical conditions (i.e., lobectomies and halvings of the organ) for some parasitic diseases (alveolococcosis, echnococcosis) and tumors, as well as for purulent processes. All experimental data characterizing the scalpel operation have been fully corroborated during the aforementioned surgery. The patients operated upon have sustained surgery successfully and recovered uneventfully. There has been observed a pronounced hemostatic effect during surgery (i.e., arresting of the parenchymatous bleeding). The hospitalization period of the patients has been cut down, too.

What is claimed is:

1. A cryogenic-and-ultrasonic scalpel, comprising:
    blade means for dissecting biological tissues, said blade means having a cutting edge;
    a body;
    vibration means for pronouncing ultrasonic vibrations, said vibration means being positioned within said body;
    a transformer positioned within said body and connected to said vibration means;
    heat exchanger means for admitting a refrigerating agent to said blade means and withdrawing said agent from said blade means for cooling the latter, said heat exchanger means positioned within said body and comprising an outside tube and at least one inside tube arranged coaxially with said outside tube, both of said tubes fluidly communicating with each other, said outside tube of said heat exchanger means communicating with said transformer and with said blade means for imparting ultrasonic vibrations from said vibration means to said blade means through said outside tube.

2. A cryogenic-and-ultrasonic scalpel as claimed in claim 1, wherein said transformer is made as a hollow annular body having a through bore coaxial with said outside tube of said heat exchanger means, while said outside tube of said heat exchanger means is positioned within said through bore.

3. A cryogenic-and-ultrasonic scalpel as claimed in claim 1, wherein a longitudinal slit is made in said outside tube of said heat exchanger means, and said blade means is tightly held in said longitudinal slit with said cutting edge extending outwardly therefrom.

4. A cryogenic-and-ultrasonic scalpel as claimed in claim 1, comprising ultrasonic vibration pickup means positioned inside said body for controlling the frequency of ultrasonic vibrations.

5. A cryogenic-and-ultrasonic scalpel as claimed in claim 2, wherein said transformer has a shape of a hollow cone frustum having a greater base and a lesser base; said greater base being connected to said vibration means and said lesser base being connected to said outside tube of said heat exchanger means so as to impart vibrations to said blade means.

6. A cryogenic-and-ultrasonic scalpel as claimed in claim 2, wherein a longitudinal slit is made in said outside tube of said heat exchanger means, and said blade means is tightly held in said longitudinal slit with said cutting edge extending outwardly therefrom.

7. A cryogenic-and-ultrasonic scalpel as claimed in claim 3 or 6, wherein said blade means has a surface that faces into said outside tube of said heat exchanger means, and at least a single-row comb is provided on said surface of said blade means.

8. A cryogenic-and-ultrasonic scalpel as claimed in claim 4, wherein said vibration means establishes an antinode zone of an ultrasonic wave, while said ultrasonic vibration pickup is located within said antinode zone.

9. A cryogenic-and-ultrasonic scalpel as claimed in claim 7, wherein said inside tube of said heat exchanger means has a plurality of holes which face towards said at least single-row comb.

10. A cryogenic-and-ultrasonic scalpel, comprising:
    blade means having a cutting edge for dissecting biological tissues;
    a body;
    vibration means for producing ultrasonic vibrations, said vibration means positioned in said body;
    a transformer positioned within said body and made as a hollow cone frustum having a greater base, lesser base, and a through bore, said greater base being connected to said vibration means;
    heat exchanger means for admitting a refrigerating agent to and withdrawing it from said blade means for cooling the latter, said heat exchanger means positioned within said body and comprising an outside tube and at least one inside tube, both fluidly communicating with each other, and said inside tube being coaxial with said outside tube;
    said outside tube of said heat exchanger means being arranged coaxially in said through bore of said transformer and connected to said lesser base of said vibration transferring member so as to impart ultrasonic vibrations to said blade means, a longitudinal slit being made in said outside tube, and said blade means being held in said longitudinal slit with said cutting edge extending outwardly therefrom;
    said blade means having a surface that faces into said outside tube of said heat exchanger means, and at least a single-row comb being provided on said surface of said blade means.

* * * * *

UNITED STATES PATENT AND TRADEMARK OFFICE
CERTIFICATE OF CORRECTION

PATENT NO. : 4,724,834

DATED : February 16, 1988

INVENTOR(S) : Alperovich, et al

It is certified that error appears in the above-identified patent and that said Letters Patent is hereby corrected as shown below:

On the Title Page:

Item [73]: "Momsk, U.S.S.R." should be --Tomsky, U.S.S.R.--

Column 6, line 26: after "into", insert --the bore of--.

Column 6, line 50: after "to", insert --said blade means--.

Signed and Sealed this

Seventh Day of February, 1989

Attest:

DONALD J. QUIGG

Attesting Officer

Commissioner of Patents and Trademarks